United States Patent
Schabbach et al.

(10) Patent No.: US 11,517,678 B2
(45) Date of Patent: Dec. 6, 2022

(54) CARTRIDGE WITH DISTRIBUTED ELECTRONIC COMPONENTS

(71) Applicant: SANOFI, Paris (FR)

(72) Inventors: Michael Schabbach, Frankfurt am Main (DE); Alexander Allerdings, Frankfurt am Main (DE); Christoph Dette, Frankfurt am Main (DE); Martin Otten, Frankfurt am Main (DE); Christian Pommereau, Frankfurt am Main (DE); Dietmar Hammen, Frankfurt am Main (DE); Paul Edward Jansen, Boston, MA (US); Ulrich Brueggemann, Bridgewater, NJ (US)

(73) Assignee: Sanofi, Paris (FR)

( * ) Notice: Subject to any disclaimer, the term of this patent is extended or adjusted under 35 U.S.C. 154(b) by 256 days.

(21) Appl. No.: 16/609,361

(22) PCT Filed: May 2, 2018

(86) PCT No.: PCT/EP2018/061113
§ 371 (c)(1),
(2) Date: Oct. 29, 2019

(87) PCT Pub. No.: WO2018/202662
PCT Pub. Date: Nov. 8, 2018

(65) Prior Publication Data
US 2020/0188598 A1 Jun. 18, 2020

(30) Foreign Application Priority Data
May 5, 2017 (EP) ..................................... 17305516

(51) Int. Cl.
*A61M 5/315* (2006.01)

(52) U.S. Cl.
CPC .... *A61M 5/31511* (2013.01); *A61M 5/31548* (2013.01); *A61M 5/31568* (2013.01);
(Continued)

(58) Field of Classification Search
CPC .......... A61M 5/31511; A61M 5/31548; A61M 5/31568; A61M 2205/3317;
(Continued)

(56) References Cited

U.S. PATENT DOCUMENTS

| 5,246,423 A | 9/1993 | Farkas |
| 5,720,733 A * | 2/1998 | Brown ....................... G01F 3/16 |
| | | 222/23 |

(Continued)

FOREIGN PATENT DOCUMENTS

| CN | 106063962 | 11/2016 |
| EP | 2190506 | 6/2010 |

(Continued)

OTHER PUBLICATIONS

Overview of materials for silicone rubber, (n.d.). Retrieved Oct. 18, 2021, from http://www.matweb.com/search/DataSheet.aspx?MatGUID=cbe7a469897a47eda563816c86a73520. (Year: 2017).*

(Continued)

*Primary Examiner* — Nilay J Shah
(74) *Attorney, Agent, or Firm* — Fish & Richardson P.C.

(57) ABSTRACT

A stopper is disclosed herein. The stopper is configured to be disposed within a medical cartridge. The stopper includes a shell defining a cavity, a core arranged within the cavity, and at least one electronic device embedded within the core, wherein the at least one electronic device includes a sensor and wherein the shell is configured to pass a sensing signal therethrough.

22 Claims, 15 Drawing Sheets

(52) U.S. Cl.
CPC ............... *A61M 2205/3317* (2013.01); *A61M 2205/3327* (2013.01); *A61M 2205/3368* (2013.01); *A61M 2205/3375* (2013.01)

(58) Field of Classification Search
CPC .... A61M 2205/332; A61M 2205/3327; A61M 2205/3375; A61M 2205/3379; A61M 5/31566; A61M 5/3157; A61M 2205/6054; A61M 5/31513
See application file for complete search history.

(56) References Cited

U.S. PATENT DOCUMENTS

| | | | |
|---|---|---|---|
| 5,921,966 A * | 7/1999 | Bendek | A61M 5/31525 604/207 |
| 6,090,081 A | 7/2000 | Sudo et al. | |
| 9,174,003 B2 | 11/2015 | Cowan et al. | |
| 2002/0016572 A1 | 2/2002 | Beebe | |
| 2003/0233075 A1 | 12/2003 | Huegli | |
| 2007/0135756 A1 | 6/2007 | Kohlbrenner et al. | |
| 2007/0219507 A1 * | 9/2007 | Dai | A61M 5/31511 604/218 |
| 2010/0016807 A1 | 1/2010 | Thilly | |
| 2012/0195182 A1 * | 8/2012 | Pommereau | A61M 5/31511 369/127 |
| 2014/0116246 A1 | 5/2014 | Melander | |
| 2014/0213975 A1 | 7/2014 | Clemente et al. | |
| 2014/0303567 A1 | 10/2014 | Qurishi et al. | |
| 2014/0330243 A1 * | 11/2014 | Kietzmann | G16H 20/17 604/500 |
| 2015/0217059 A1 | 8/2015 | Ashby et al. | |
| 2016/0022539 A1 | 1/2016 | Daines | |
| 2017/0312445 A1 | 11/2017 | Mirov et al. | |
| 2017/0316177 A1 * | 11/2017 | Mirov | B23P 15/00 |
| 2018/0193567 A1 * | 7/2018 | Schleicher | A61M 5/1684 |
| 2020/0114088 A1 | 4/2020 | Schabbach et al. | |
| 2021/0001053 A1 | 1/2021 | Kuehn | |

FOREIGN PATENT DOCUMENTS

| | | | |
|---|---|---|---|
| JP | H10-314305 | 12/1998 | |
| JP | 2004162761 A * | 6/2004 | ........ A61M 5/31513 |
| JP | 2006-078076 | 3/2006 | |
| JP | 2007-509652 | 4/2007 | |
| JP | 2007-160095 | 6/2007 | |
| JP | 2010-007178 | 1/2010 | |
| JP | 2016-510241 | 4/2016 | |
| WO | WO 2001/097885 | 12/2001 | |
| WO | WO 2009/024562 | 2/2009 | |
| WO | WO 2009/032399 | 3/2009 | |
| WO | WO 2013/064590 | 5/2013 | |
| WO | WO 2014/128155 | 8/2014 | |
| WO | WO 2014/145906 | 9/2014 | |
| WO | WO-2016036574 A1 * | 3/2016 | .......... A61M 5/1684 |
| WO | WO 2016/113409 | 7/2016 | |
| WO | WO 2017/070391 | 4/2017 | |

OTHER PUBLICATIONS

Dielectric Manufacturing. (Jun. 2, 2021). Material properties of teflon-polytetrafluoroethylene. Dielectric Manufacturing. Retrieved Oct. 18, 2021, from https://dielectricmfg.com/knowledge-base/teflon/. (Year: 2019).*

International Preliminary Report on Patentability in Application No. PCT/EP2018/061113, dated Nov. 5, 2019, 9 pages.

International Search Report and Written Opinion in Application No. PCT/EP2018/061113, dated Jun. 25, 2018, 12 pages.

International Preliminary Report on Patentability in Application No. PCT/EP2018/061110, dated Nov. 5, 2019, 8 pages.

International Search Report and Written Opinion in Application No. PCT/EP2018/061110, dated Jun. 13, 2018, 11 pages.

* cited by examiner

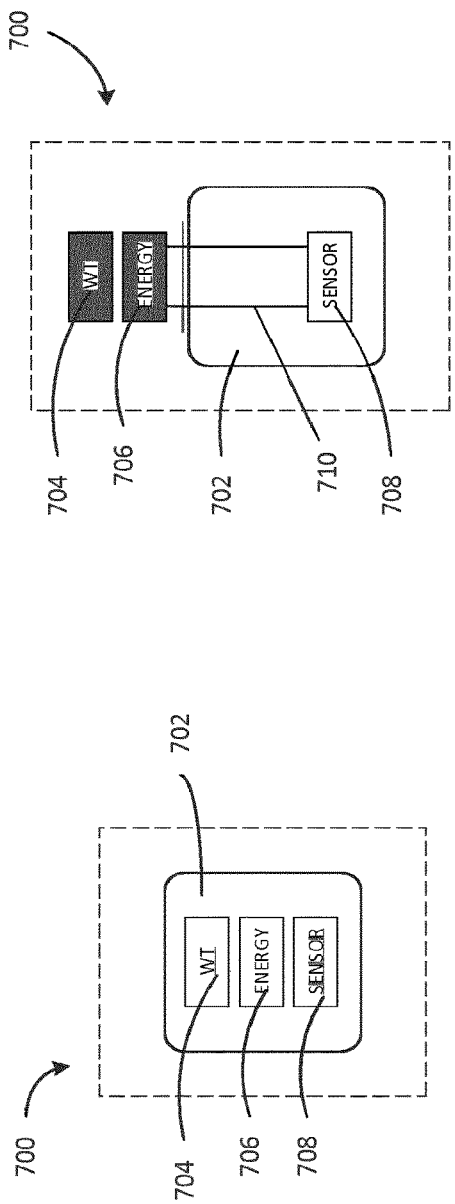
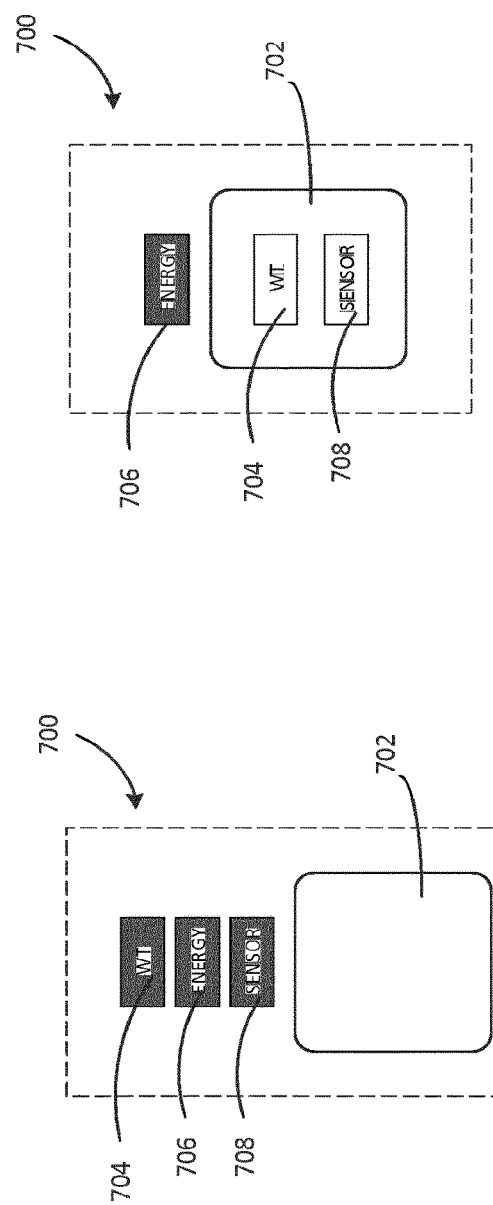
FIG. 7A
FIG. 7B
FIG. 7C
FIG. 7D

CARTRIDGE WITH DISTRIBUTED ELECTRONIC COMPONENTS

CROSS REFERENCE TO RELATED APPLICATIONS

The present application is the national stage entry of International Patent Application No. PCT/EP2018/061113, filed on May 2, 2018, and claims priority to European Patent Application No. 17305516.1, filed on May 5, 2017, the disclosures of which are incorporated herein by reference.

TECHNICAL FIELD

This description relates to an apparatus for a medical device configured to eject a medicament, and more particularly to a stopper for a manually operable injection device.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of drug doses, for example once or several times per day. For instance, a pre-filled disposable drug pen or autoinjector can be used as an injection device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

SUMMARY

According to a first aspect of the present disclosure, there is provided a stopper configured to be disposed within a medical cartridge, the stopper including a shell defining a cavity, a core arranged within the cavity, and at least one electronic device embedded within the core, wherein the at least one electronic device includes a sensor and wherein the shell is configured to pass a sensing signal therethrough.

The stopper may include a shell that thermally insulates the at least one embedded electronic device such that the stopper can be heat sterilized. The stopper may be heat sterilized at a temperature of at least 120 degrees Celsius for at least 20 minutes. The stopper may include a shell that is substantially rigid and a core that is substantially soft. The stopper may include a cover configured to interface with the shell such that a mechanical force may be transmitted therethrough with limited compression of the core. The stopper may include a shell that is substantially soft and a core that is substantially rigid. The at least one embedded electronic device may communicate with at least one electronic device located external to the stopper. The sensing signal may be an electromagnetic signal or an acoustic signal. The sensor may include a piezoelectric device. The at least one embedded electronic device may include an energy source.

The stopper may include a shell and a core that are substantially inseparable. The at least one embedded electronic device may include a wireless transceiver. The wireless transceiver may be configured to transmit data acquired by the sensor to an electronic device external to the stopper.

According to another aspect, there is provided a cartridge including a cartridge housing, a stopper configured to be disposed within the cartridge housing, the stopper including a shell defining a cavity, a core sized and shaped to fit within the cavity of the shell, and at least one embedded electronic device embedded within the core, wherein the at least one electronic device includes a sensor and wherein the shell is configured to pass a sensing signal therethrough, and at least one external electronic device located external to the stopper wherein the at least one external electronic device is configured to communicate with the at least one embedded electronic device.

The at least one external electronic device may be located in a threaded rod area of the cartridge. The cartridge housing may be configured for use with an autoinjector.

In another aspect, there is provided a method of manufacturing a medical cartridge including embedding at least one electronic device into a core of a stopper, coupling the core with a shell, the shell providing heat resistance to the at least one electronic device embedded in the core, sterilizing the stopper via heat sterilization, and assembling the stopper into the cartridge.

Advantages of these techniques include the following aspects. In some embodiments, electronic components are distributed in the cartridge which may save space or eliminate the need for an external device coupled to an injector pen. In some embodiments, one or more electronic components may be embedded within the stopper, which may further save space.

In some embodiments, it is an advantage to have at least one electronic component embedded in the stopper as the manufacturing and sterilization process is simple and reduces assembly complexity. In other embodiments, a sensor is embedded in the stopper which places it in an advantageous location to take position-based measurements. The position based measurements allow for dosage information, including volume, to be computed.

In some embodiments, a heat resistance provided by a shell (or a core) of the stopper allows heat sensitive electronics to be embedded in the core and undergo heat sterilization. As the electronics may be embedded, the stopper may be heat sterilized as one-piece or may be embedded in the cartridge prior to heat sterilization, allowing for a simple assembly process.

The details of one or more embodiments are set forth in the accompanying drawings and the description below. Other features, objects, and advantages will be apparent from the description and drawings, and from the claims.

BRIEF DESCRIPTION OF THE FIGURES

FIG. 7A is a schematic view of a distributed electronics system for a medical cartridge where a wireless transceiver, an energy source, and a sensor are disposed within the stopper.

FIG. 7B is a schematic view of a distributed electronics system for a medical cartridge where the sensor is disposed within the stopper and connected to an external energy source via at least one lead.

FIG. 7C is a schematic view of a distributed electronics system for a medical cartridge where the wireless transceiver, energy source, and sensor are disposed external to the stopper.

FIG. 7D is a schematic view of a distributed electronics system for a medical cartridge where the wireless transceiver and the sensor are disposed within the stopper and the energy source is disposed external to the stopper.

Like reference symbols in the various drawings indicate like elements.

DETAILED DESCRIPTION

Cartridge-based injection and medical syringe systems may be difficult to sterilize prior to use if they include electronics in the replaceable portions of the device (e.g. a cartridge stopper or a cartridge housing). In some examples of the present disclosure, the cartridge stopper can be heat sterilized with electronic components embedded inside. For example, a stopper at least partially made of a heat resistive material, or coated with a heat resistant coating, may provide protection to embedded electronic components during a heat sterilization process. Some examples also enable adding or connecting additional electronic components (e.g. an energy source) to a heat sterilized stopper with at least one electronic component embedded inside.

Figure 1:
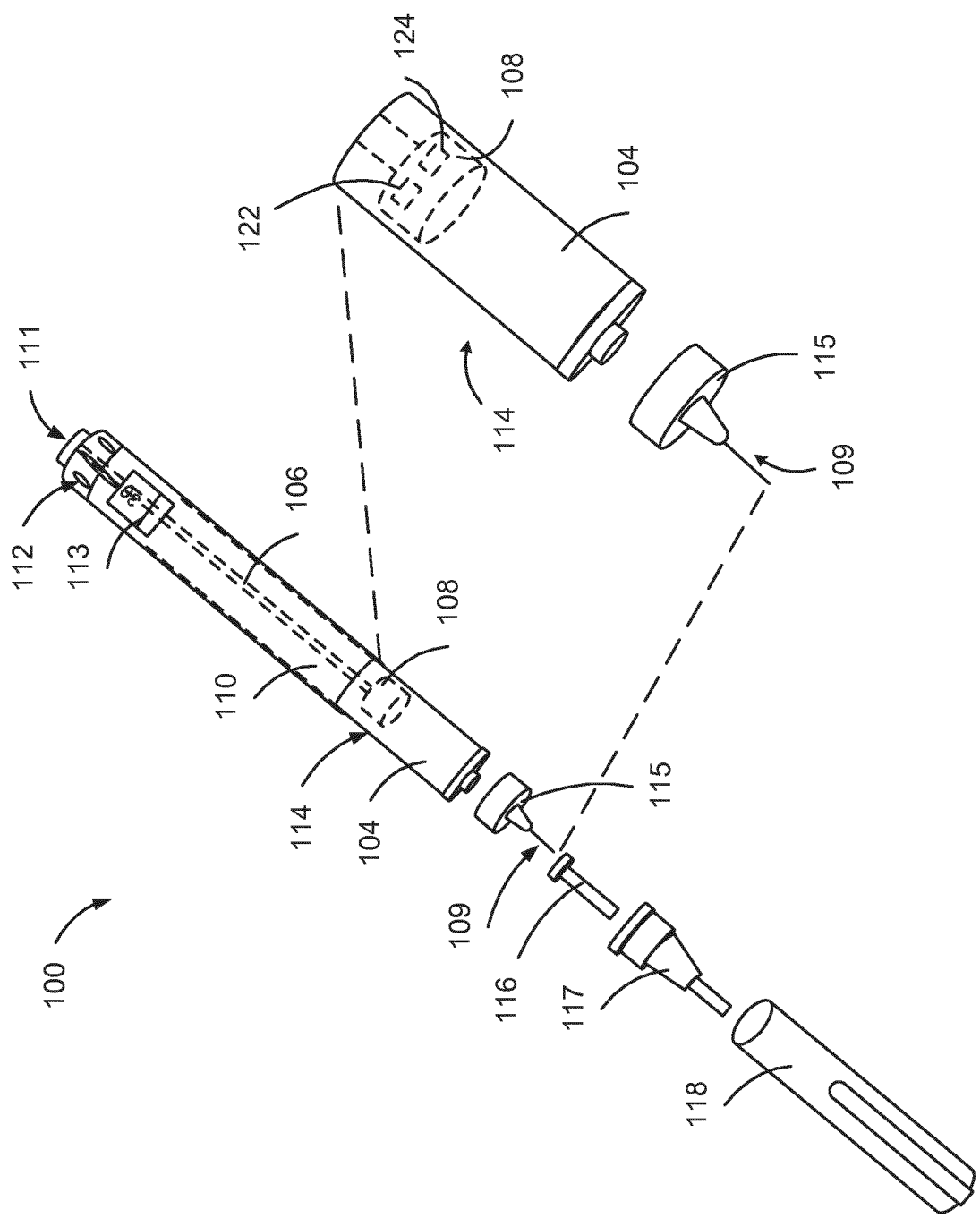
FIG. 1 is an exploded view of an injection device.

FIG. 1 is an exploded view of an injection device 100. The injection device 100 of FIG. 1 is a pre-filled disposable injection pen that includes a housing 110 and a having therein a cartridge 114 with cartridge housing 104, to which a needle assembly 115 can be affixed. The needle 109 of needle assembly 115 is protected by an inner needle cap 116 and an outer needle cap 117, which in turn can be covered by cap 118. A medicament dose to be ejected from the injection device 100 can be selected by turning a dosage knob 112, and the selected dose is then displayed via a dosage window or display 113. The display can include a digital display, for example. It will be understood that dosage window 113 relates to the section of the injection device 100 through or on which the selected dosage is visible.

As described further below, the injection device 100 may include one or more electronic components 122, 124, some of which may be included in the stopper 108, for example, and some of which may be included outside of the stopper 108.

Turning the dosage knob 112 causes a mechanical click sound to provide acoustical feedback to a user. The numbers displayed in the dosage display 113 are printed on a sleeve that is contained in the housing 110 and mechanically interacts with a piston in the cartridge 114. When the needle 109 is stuck into a skin portion of a patient, and then the injection button 111 is pushed, the insulin dose displayed in display 113 will be ejected from the injection device 100. During an injection, a drive mechanism 106, which is shown as an outline of a plunger arm, drives a stopper 108 into the cartridge to expel the drug (e.g. cartridge 114). When the needle 109 of the injection device 100 remains for a certain time in the skin portion after the injection button 111 is pushed, a high percentage of the dose is actually injected into the patient's body.

The injection device 100 may be disposable or removable.

Figure 2B:
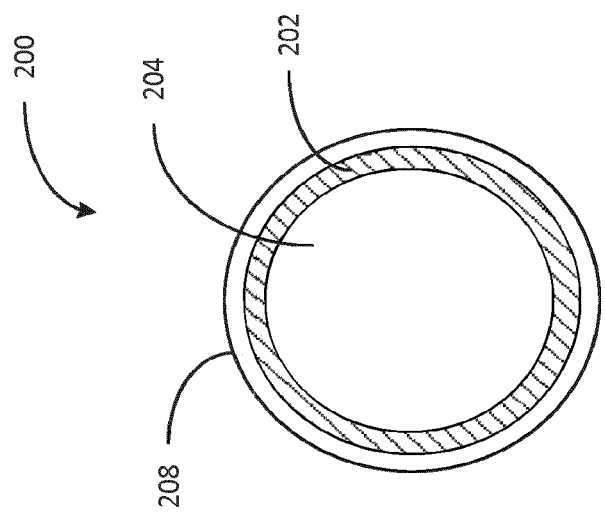
FIG. 2B is a top view of the stopper of FIG. 2A.
Figure 2A:
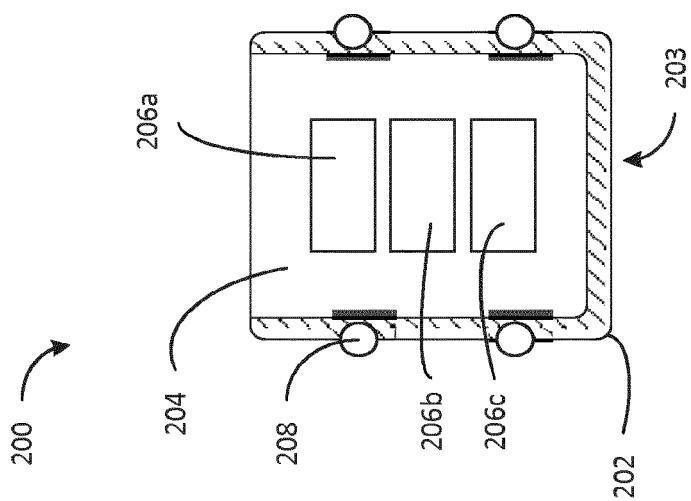
FIG. 2A is a cross sectional view of a stopper configured to be disposed in an injection device, the stopper having a rigid shell and a soft core with electronic devices embedded in the core.

FIG. 2A is a cross sectional view of an embodiment of a stopper 200 configured to be disposed in an injection device (e.g., the injection device 100), the stopper 200 having a rigid shell 202 and a soft core 204 with electronic devices embedded in the core. The stopper 200 includes a substantially rigid shell 202 and a substantially soft core 204. In this embodiment, the shell 202 and the core 204 are substantially inseparable after manufacturing. By "substantially inseparable," we mean that the core 204 and the shell 202 would undergo an irreversible decoupling were they to be separated. For example, the core 204 and the shell 202, when they are substantially inseparable may not be separated by simply popping the core 204 out of the shell 202.

For example, the core 204 may be formed upon filling shell 202 with a substantially soft material that hardens when exposed to air or a chemical agent (e.g. by pouring, injecting, etc. the substantially soft material). For example, the substantially soft material may be epoxy, resin, or another soft material that hardens. Due to this filling process, the core 204 would be difficult to remove from the shell 202 as they would be integrated as one piece. The core 204 contains embedded electronic devices 206a, 206b, and 206c. In one embodiment, the electronic devices 206a, 206b, and 206c may be inserted into the cavity of the shell 202 and then a substantially soft material may be introduced into the cavity to surround the electronic devices 206a, 206b, and 206c and form the core 204. Shell 202 interfaces with sealing element 208 (e.g. an o-ring) to provide a sealing interface with the cartridge upon the stopper's introduction into the cartridge.

Figure 2C:
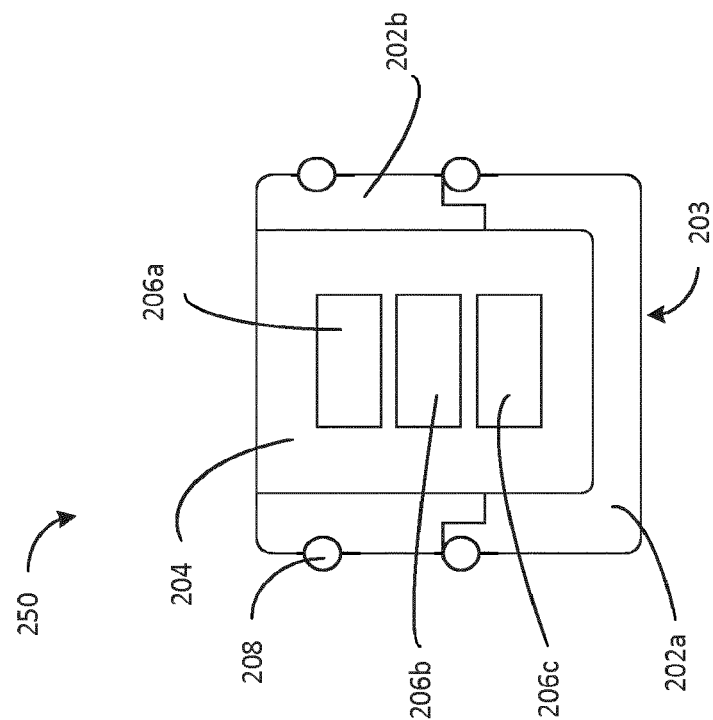
FIG. 2C is another example of a stopper.

The materials selected for the shell 202 and the core 204 are selected based on their hardness, elasticity, and their heat resistive or insulating properties. In some embodiments, the shell 202 and the core 204 are made of polymer materials with varying elastic properties. In some embodiments, heat resistive coatings may also be applied to the core 204 to increase heat resistance, such as, for example, a polytetrafluoroethylene (PTFE), also known as Teflon, coating. In some cases, the shell could be made of material which is selected to be compatible with the medicament e.g. PP, PE, POC, POP, PTFE or butyl rubber at the surface 203 which is in contact with the medicament. Alternative to coating, as shown in FIG. 2C, the compatible material could be comolded or assembled (e.g., using snap features) with another material such that the compatible material forms a first portion 202*a* of the shell that contacts the medicament at surface 203 and another material forms a second portion 202*b* of the shell not in contact with the medicament. The materials selected for the shell 202 and the core 204 are also selected for their ability to allow a sensor signal to pass through.

The embedded electronic devices may include, for example, a sensor, an energy source, a microcontroller, a wireless transceiver, and an energy harvesting device. The embedded electronics 206*a*, 206*b*, and 206*c* are representative only. There can be any number of embedded electronics. The sensor may be a sensor/transceiver device such as, for example, a piezoelectric device. A sensor/transceiver may transmit a sensing signal, such as, for example, an ultrasonic, acoustic, light, or other signal, through the stopper and measure a response. An acoustic signal may include mechanical or vibrational energy. The response received could be provided to a controller (e.g. an embedded or an external microcontroller) which may receive the response and calculate a state of the cartridge. The state of the cartridge may correspond to, for example, a fill level of medicament in the cartridge or a position of the stopper. The state of the cartridge may allow measurement of an injected dose of medicament.

The energy sources can be a battery, a device generating energy by loading a capacitor, be solar powered, or the like. The wireless transceiver may communicate with an external electronic device as well as with the sensor and energy source. The external electronic device, which may be the controller, may communicate data received from the sensor to an external database. The wireless transceiver may communicate using any known wireless communication technique including, for example Bluetooth, NFC, or radio frequencies. The communication with the controller can be one way or bidirectional. In some embodiments, data transferred from the sensor device to an external data base contains information which is related to the identity of the device e.g. a unique number, calibration data, production lot information, device material information, data related to storage time and production time, and information related to the sensor measurement (e.g., time of measurement, sensor measurement results like temperature, distances, light signals, acoustic signals). In some embodiments, data coming from the external data base device to the controller contains information regarding "wake up" signals, triggers to measure, time information, or calibration data.

FIG. 2B is a top view of the stopper 200 of FIG. 2A. Shell 202 surrounds core 204 and interfaces with sealing element 208, which forms a sealing interface with the cartridge upon the stopper's 200 introduction into the cartridge. The sealing interface may form at least part of a sterile barrier within the cartridge which is required to preserve the sterility of the medicament to be delivered by the injection device.

The shell 202, in some embodiments, is constructed from of a rigid material such as metal, polymer (e.g., COC, PA, PP, PE, POM, PS, ABS, COP, etc.), glass or ceramics. In some embodiments, the electronic devices (or electronic assembly) 206*a*, 206*b*, 206*c* includes one or more of the following: a sensor, a power source (e.g. battery), a controller, a wireless communication module (e.g. Bluetooth, NFC, Bluetooth LE, any RF, IrDA, Acoustic module, memory, on-off switch, thermo-sensing element, pressure sensor etc. In some embodiments, the sealing members 208 are made from a first material and the shell 202 is made from a second material of lower compressibility compared to the first members material, and where the shell 202 is formed as a receptacle to house the core 204. In some embodiments, the electronic devices 206*a*, 206*b*, 206*c* and the core 204 and are connected to the shell 202 using snap features, glue, welding, US welding, thermal welding or other means. In some embodiments, the core 204 is removably coupled to the shell 202. In some embodiments, the sealing member 208 is made of a natural rubber or any biocompatible composition of rubber. In some embodiments, the core 204 includes an on-off switch configured to trigger the electronics devices 206*a*, 206*b*, 206*c* by any suitable impact on the stopper 200 (e.g. force from a drive mechanism 106)

Figure 2D:
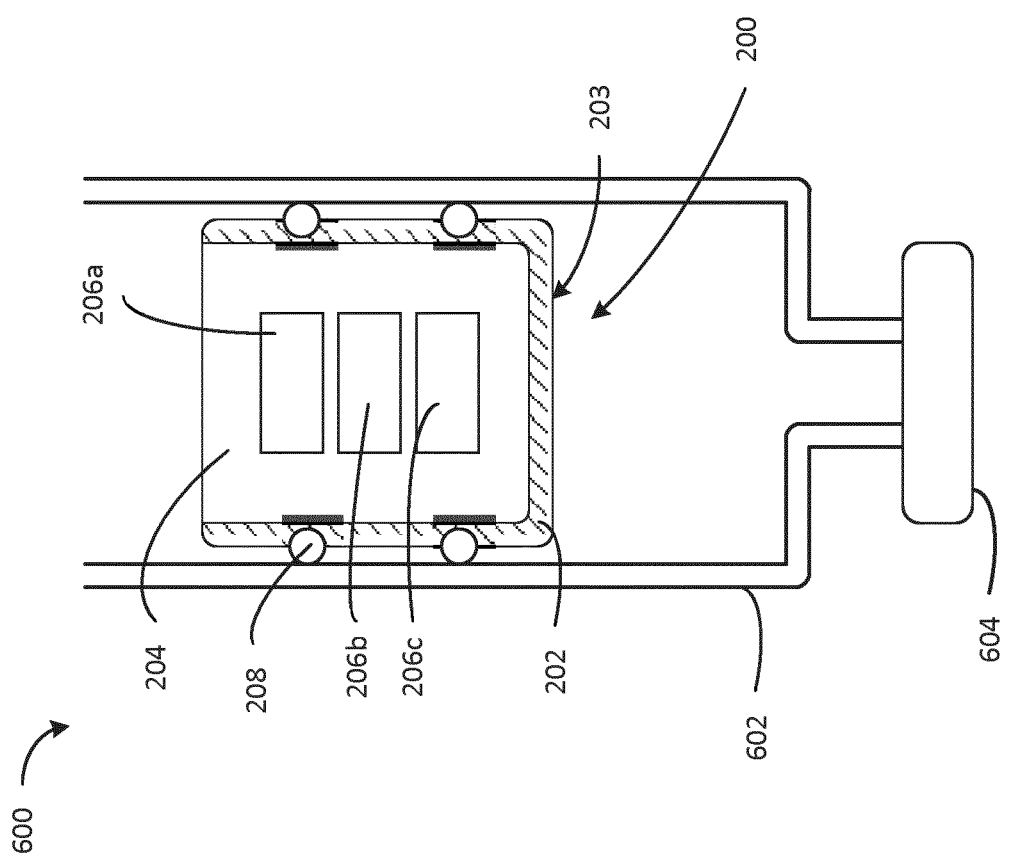
FIG. 2D is a cross-sectional view of a stopper disposed within a cartridge.

FIG. 2D is a cross-sectional view of a stopper 200 disposed within a cartridge 600. The various features of the stopper 200 shown are described above with respect to FIGS. 3A and 3B. The stopper 200 may be replaced by any stopper of the following figures, which would interface with the cartridge 600 in much the same fashion as will be described here for stopper 300. The cartridge 600 includes a housing 602 which interfaces with the sealing element 208 of the stopper 200 to seal an open end of the cartridge 600. In some embodiments, a medicament (e.g., a medical fluid or drug) is disposed in the space between the cap 604 of the cartridge 600 and the shell 202 of the stopper 200. In some embodiments, the embedded electronics 206*a*, 206*b*, and 206*c*, include a sensor configured to send and receive a signal to sense a position of the stopper 200 in the cartridge 600.

In an example, a transmitter (e.g., one of the electronics devices 206*a*, 206*b*, and 206*c*) transmits an acoustic wave at a first time t1. The first time t1 (e.g., the transmission time of the acoustic wave) may be provided to an external device. The acoustic wave propagates from the transmitter in the stopper 200 toward the distal end of the cartridge 600 and is reflected off of (e.g., bounces off of) a surface of the cartridge 600 or a reflector (not shown). A reflection of the acoustic wave (e.g., a reflected wave) propagates from the distal end of the cartridge 600 (i.e., the end having the cap 604) toward a sensor in the stopper 200. The reflected wave is received at a second time t2. The speed of the acoustic wave is a known speed of sound in the medicament in the cartridge. The elapsed time between transmission and receiving of the acoustic wave is t2-t1. The elapsed time is multiplied by the speed of sound to determine the distance traveled by the wave from the transmitter, to the distal end of the cartridge 600, back to the sensor. The distance traveled is divided by two to determine the distance between the stopper 200 and the distal end of the cartridge 600. The volume of medicament in the cartridge 600 (e.g., the volume of medicament enclosed in the cartridge 600 between the stopper 200 and the proximal end) is determined by multiplying the determined distance by the cross-sectional area of the cartridge 600. The difference between the determined volume of medicament in the cartridge 600 before and after dosing corresponds to the dose administered to the patient.

Figure 3B:
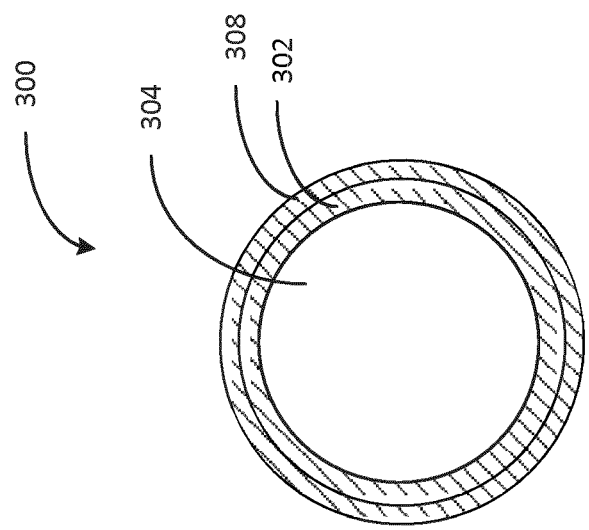
FIG. 3B is a top view of the stopper of FIG. 3A.
Figure 3A:
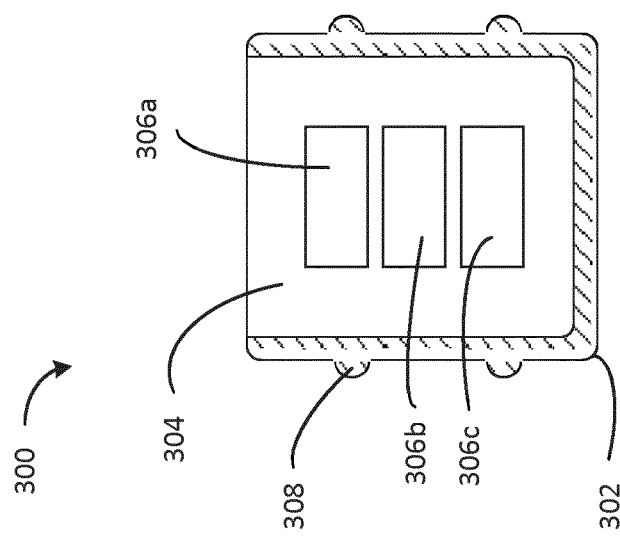
FIG. 3A is a cross sectional view of a stopper configured to be disposed in an injection device, the stopper having a soft shell and a rigid core with electronic devices embedded in the core.

FIG. 3A is a cross sectional view of a stopper 300 configured to be disposed in an injection device 100, the stopper 300 having a soft shell 302 and a rigid core 304 with electronic devices 306*a*, 306*b*, 306*c* embedded in the core 304. In some embodiments, the rigid core 304 has the advantage to protect the electronics devices 306*a*, 306*b*, 306*c* from getting deformed by the push of the plunger. This ensures reliable sensor signals. Another advantage is the rigid core 304 leads to better injection dose accuracy because of less elastic effects from the stopper 300 during injection. This also helps to shorten the holding time during injection. Soft in this context of the soft shell 302 means an visco-elastic material, for example, natural rubber, thermoplastic elastomers (TPE), butyl rubber, neoprene, fluroelastomers, silicone rubber etc., which are characterized by a low e-module (high elastic deformation and low remaining deformation and stress). The stopper 300 includes a substantially soft shell 302 and a substantially rigid core 304. In this embodiment, the shell 302 and the core 304 are substantially inseparable after manufacturing. For example, the shell 302 may be formed by molding the shell 302 around the substantially rigid core 304 using a substantially soft material (e.g. by pouring, injecting, etc. the substantially soft material). The core 304 contains embedded electronic devices 306a, 306b, and 306c. In one embodiment, the substantially rigid material may be molded around electronic devices 306a, 306b, and 306c while it is in an uncured, softened state and may solidify to form the rigid core 304. In another embodiment, the electronic devices 306a, 306b, 306c may be introduced into the substantially rigid material while it is in an uncured, softened state before the substantially rigid material solidifies to form the rigid core 304. Integrated sealing element 308 is configured to provide a sealing interface between the stopper and an interior wall of the cartridge upon the stopper's introduction into the cartridge.

The soft shell 502 has the advantage it has the shell function and sealing function in one component. However, in a manufacturing process it may be more difficult to handle a soft or elastomeric shell material for assembly. A rigid shell is easier to handle/hold during the manufacturing process and may lead to better dosing accuracy but requires separate sealing element like o-rings to provide the sealing interface to the cartridge. A substantially rigid core has the advantage of easier handling during manufacturing and better protection of possible stress sensitive sensor elements.

The various materials from which the shell 302 and the core 304 could be produced as well as the various electronic devices that may be embedded in the core are described above with respect to FIG. 2A. Additionally, the material for the shell may be medical grade with the stopper being configured to come in contact with the medicament.

FIG. 3B is a top view of the stopper of FIG. 3A. Shell 302 surrounds core 304 and includes an integrated sealing element 308, which forms a sealing interface with the cartridge upon the stopper's introduction into the cartridge. The sealing interface may form at least part of a sterile barrier within the cartridge which is required to preserve the sterility of the medicament to be delivered by the injection device.

The one piece stoppers of FIGS. 2A, 2B, 3A, and 3B may be sterilized, for example, by using a heat sterilization process. In an example heat sterilization process, the stopper would be sterilized at a temperature of approximately 120 degrees Celsius for between approximately twenty and thirty minutes.

The core 304, in some embodiments, is constructed from of a rigid material such as metal, polymer (e.g., COC, PA, PP, PE, POM, PS, ABS, COP, etc.), glass or ceramics. In some embodiments, the electronic devices (or electronic assembly) 306a, 306b, 306c includes one or more of the following: a sensor, a power source (e.g. battery), a controller, a wireless communication module (e.g. Bluetooth, NFC, Bluetooth LE, any RF, IrDA, Acoustic module, memory, on-off switch, thermo-sensing element, pressure sensor etc. In some embodiments, the sealing members 308 are made from a first material and the shell 302 is made from a second material of lower compressibility compared to the first members material, and where the shell 302 is formed as a receptacle to house the core 304. In some embodiments, the electronic devices 306a, 306b, 306c and the core 304 and are connected to the shell 302 using snap features, glue, welding, US welding, thermal welding or other means. In some embodiments, the core 304 is removably coupled to the shell 302. In some embodiments, the sealing member 308 is made of a natural rubber or any biocompatible composition of rubber. In some embodiments, the core 304 includes an on-off switch configured to trigger the electronics devices 306a, 306b, 306c by any suitable impact on the stopper 300 (e.g. force from a drive mechanism 106).

Figure 4:
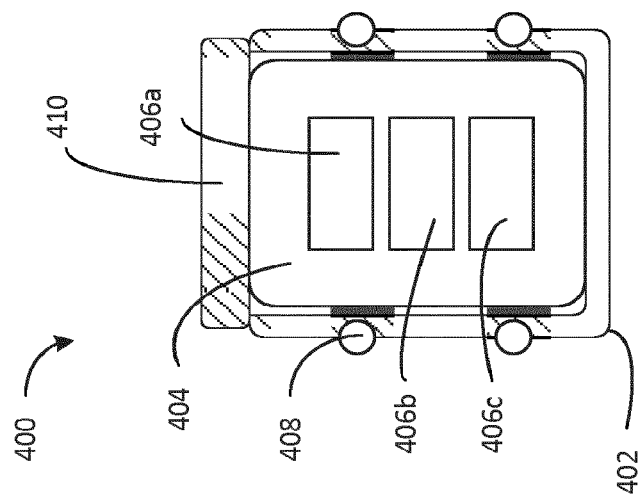
FIG. 4 is a cross-sectional view of a stopper configured to be disposed in an injection device, the stopper having a rigid shell and a soft insertable core with electronic devices embedded in the core and having a rigid cover.

FIG. 4 is a cross-sectional view of a stopper 400 configured to be disposed in an injection device 100, the stopper 400 having a rigid shell 402 and a soft insertable core 404 with electronic devices 406a, 406b, 406c embedded in the core 404 and having a rigid cover 410. Stopper 400 includes a substantially rigid shell 402 and a substantially soft core 404. In this embodiment, the shell 402 and the core 404 are manufactured separately and the core 404 is inserted into the shell 402 in a subsequent assembly step. For example, the core 404 may be formed upon filling a mold with a substantially soft material (e.g. by pouring, injecting, etc. the substantially soft material) and embedding electronic devices 406a, 406b, and 406c before the substantially soft material sets (e.g. cures, solidifies, etc.). In another embodiment, the substantially soft material is introduced surrounding the electronic devices 406a, 406b, and 406c and shaped (e.g. cut, poured into a mold, etc.) to form the core 404. Shell 402 interfaces with sealing element 408 in order to provide a sealing interface with the cartridge upon the stopper's introduction into the cartridge.

Figures 11A, 11B:
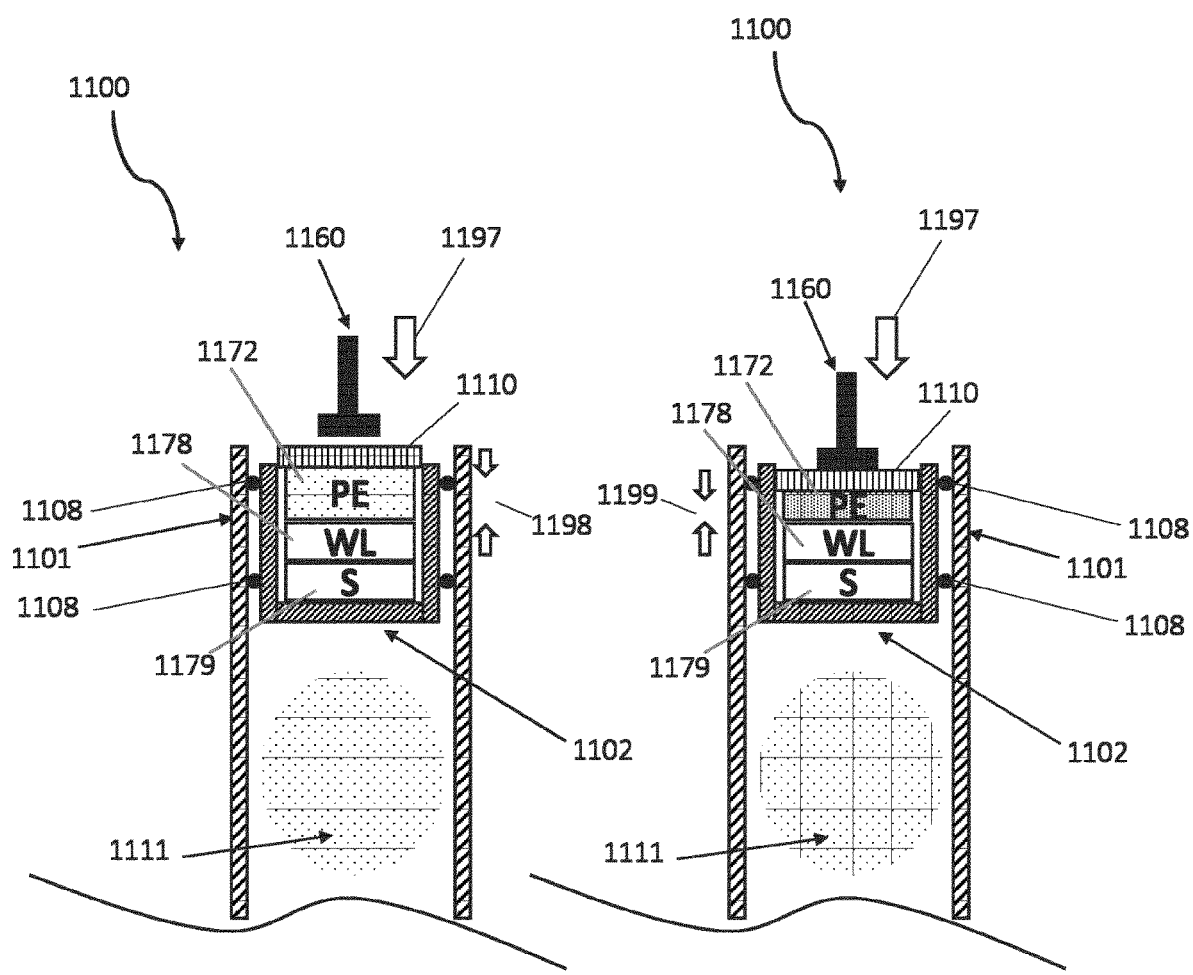
FIGS. 11A and 11B are cross-sectional views of a stopper disposed within a cartridge and communicating with a piezoelectric system.

Stopper 400 also includes a substantially rigid cover 410 configured to interface with the substantially rigid shell 402 and with a plunger 1160 (FIGS. 11A and 11B). The plunger imparts a force to the cover 410 which is configured to transfer the force to the substantially rigid shell 402. The force transfer would be significantly reduced if the cover 410 is removed as the plunger may deform (e.g. by compressing) the substantially soft core 404. Limited compression of the core 404, meaning that the core is not deformed more than 5% in the direction of plunger travel, allows for more efficient force transfer between the stopper 400 and the plunger. The cover 410 also provides a beneficial geometry for interfacing with the plunger as it contacts a top surface of the rigid shell 402 along the circumference of the shell 402. Though the plunger head may be sized to make contact with the top surface of the shell 402 (e.g. the diameter of the plunger is larger than the diameter of the cavity of the shell), including a cover 410 may allow the force to be more evenly distributed on the shell.

Figure 5:
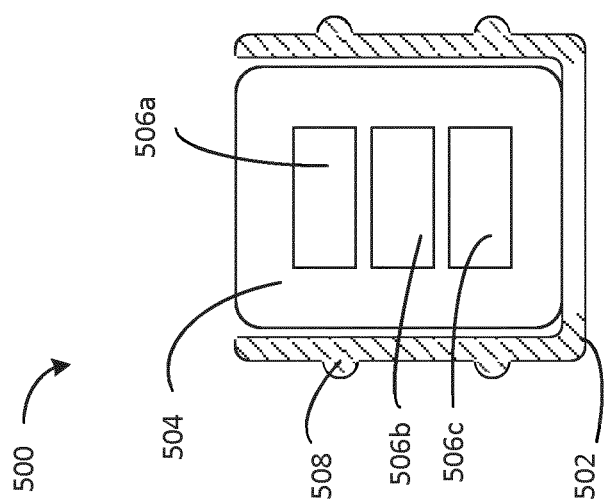
FIG. 5 is a cross-sectional view of a stopper configured to be disposed in an injection device, the stopper having a soft shell and a rigid insertable core with electronic devices embedded in the core.

FIG. 5 is a cross-sectional view of a stopper configured to be disposed in an injection device, the stopper having a soft shell and a rigid insertable core with electronic devices embedded in the core. Stopper 500 includes a substantially soft shell 502 and a substantially rigid core 504. In this embodiment, the shell 502 and the core 504 are manufactured separately and the core 504 is inserted into the shell 502 in a subsequent assembly step. For example, the core 504 may be formed upon filling a mold with a substantially rigid material (e.g. by pouring, injecting, etc. the substantially rigid material) and embedding electronic devices 506a, 506b, and 506c before the substantially rigid material sets (e.g. cures, solidifies, etc.). In another embodiment, the substantially rigid material is introduced surrounding the electronic devices 506a, 506b, and 506c and shaped (e.g. cut, poured into a mold, etc.) to form the core 504. Integrated sealing element 508 is configured to provide a sealing interface with the cartridge upon the stopper's introduction into the cartridge.

The cores 404 and 504 of the two-piece stoppers of FIG. 4 and FIG. 5 may be inserted after the shells 402 and 502 have been inserted into the cartridge. The shell and cartridge may be heat sterilized. The cores 404 and 504, including their embedded electronics, may be pushed inside the cavity formed by the shell of the stopper after the cartridge has been sterilized.

Figure 6:
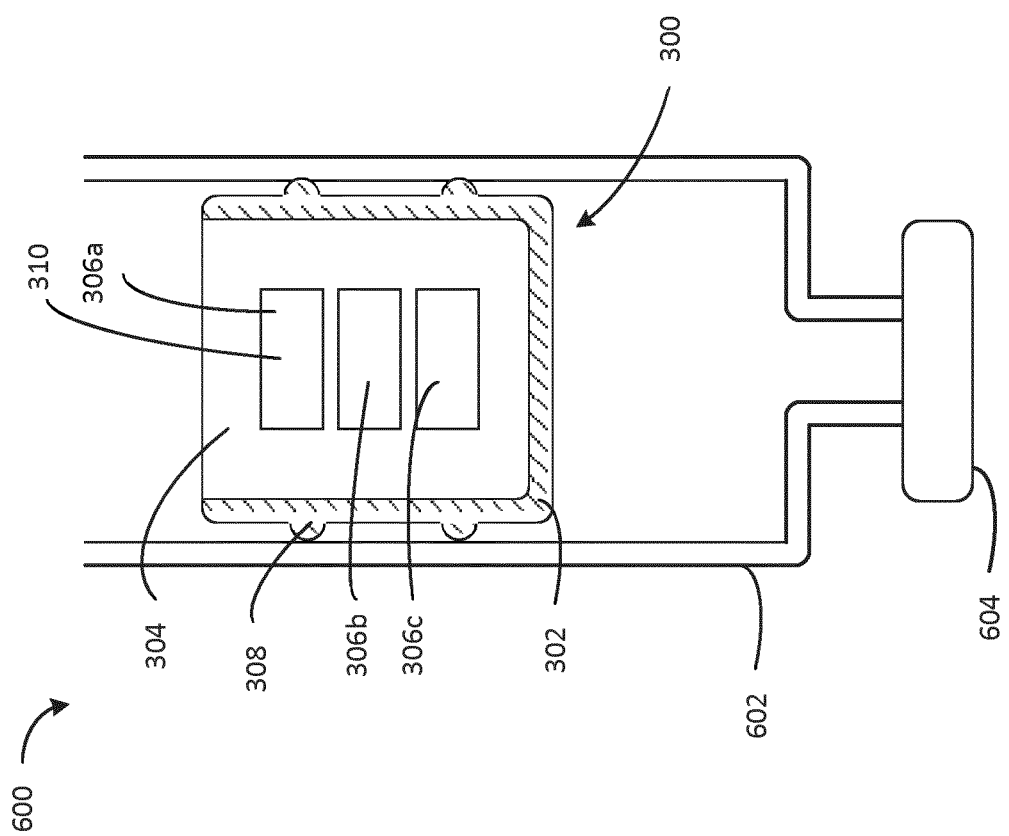
FIG. 6 is a cross-sectional view of a stopper disposed within a cartridge.

FIG. 6 is a cross-sectional view of a stopper disposed within a cartridge. The various features of the stopper shown are described above with respect to FIGS. 3A and 3B. The stopper 300 may be replaced by any stopper of the previous figures, which would interface with the cartridge in much the same fashion as will be described here for stopper 300. The cartridge 600 includes a housing 602 which interfaces with the sealing element 308 of the stopper 300. The medicament may be disposed in the space between the cap 604 of the cartridge and the shell 302 of the stopper. The embedded electronics 306a, 306b, and 306c, may include a sensor 310 which may send and receive a sensing signal to sense a position of the stopper 300 in the cartridge 600.

The sensor 310 may be a sensor/transceiver device such as, for example, a piezoelectric device. A sensor/transceiver may transmit a sensing signal, such as, for example, an ultrasonic, acoustic, light, or other signal through the stopper 300 and measure a response. One implementation of determining dosage based on transmitting an acoustic sensing signal and measuring a response is described above with respect to FIG. 2D. The response received could be provided to a controller (e.g. an embedded or an external microcontroller) which may receive the response and calculate a state of the cartridge 600. The state of the cartridge 600 may correspond to, for example, a fill level of medicament in the cartridge 600 or a position of the stopper 300. The state of the cartridge may allow measurement of an injected dose of medicament. In some embodiments, different measuring methodologies are used to measure the position of the stopper 300 as described. A certain signal needs to be generated, which changes with the movement of the stopper 300 relative to a fixed position in the system or cartridge 600. This fixed position can be inside of the cartridge 600 e.g., the septum area of a cartridge 600 which never moves or another rigid wall of the cartridge 600, or an element which may be introduced into the cartridge for this purpose or the reference could be outside of the cartridge outside e.g. an element of the injection device like a housing part. In some embodiments, a sensor measures the change of a light signal with sending out the light from a light source (e.g., an LED) to the fixed area and receiving the remitted light with a photodetector. The intensity of the remission can be correlated to a distance. Another possibility is to measure the change of time needed for the signal (e.g. acoustic signal) to travel from a sender to the fixed position back to a receiver positioned close to the sender. In another embodiment, the signal (optical, acoustic, capacitive etc.,) can be sent out from a fixed position to a receiver in the moving stopper 300 to measure the change of the signal during stopper travel and correlate it to the stopper position in the cartridge 600.

The schematics shown in FIGS. 7A-7D describe the locations and orientations of the various electronic components with respect to the stopper 702. FIG. 7A is a schematic view of a distributed electronics system 700 for a medical cartridge 600 where a wireless transceiver 704, an energy source 706, and a sensor 708 are disposed within the stopper 702. In this embodiment, the stopper includes three embedded electronic devices and the cartridge 600 does not contain external electronic devices in communication with the embedded electronic devices. When no external electronic devices are required, space can be saved in the cartridge and/or the need for an external device coupled to the injector pen can be eliminated, simplifying assembly. Additionally, the cartridge is more easily assembled when all of the required electronic components are included in the stopper.

FIG. 7B is a schematic view of a distributed electronics system 700 for a medical cartridge 600 where the sensor 708 is disposed within the stopper 702 and connected to an external energy source 706 via at least one connector 710. In this embodiment, the sensor 708 must be electrically connected to the energy source 706 so the energy source 706 can provide power to the sensor 708. In this embodiment, the electrical connection is accomplished by wiring the sensor and the energy source to one another with connector 710. These wires may be embedded in the core or the shell of the stopper 702 (FIG. 2A). This embodiment allows the stopper to be heat sterilized, yet allows for the use of an energy source 706 that may not withstand the heat sterilization process of the stopper.

Figure 8A:
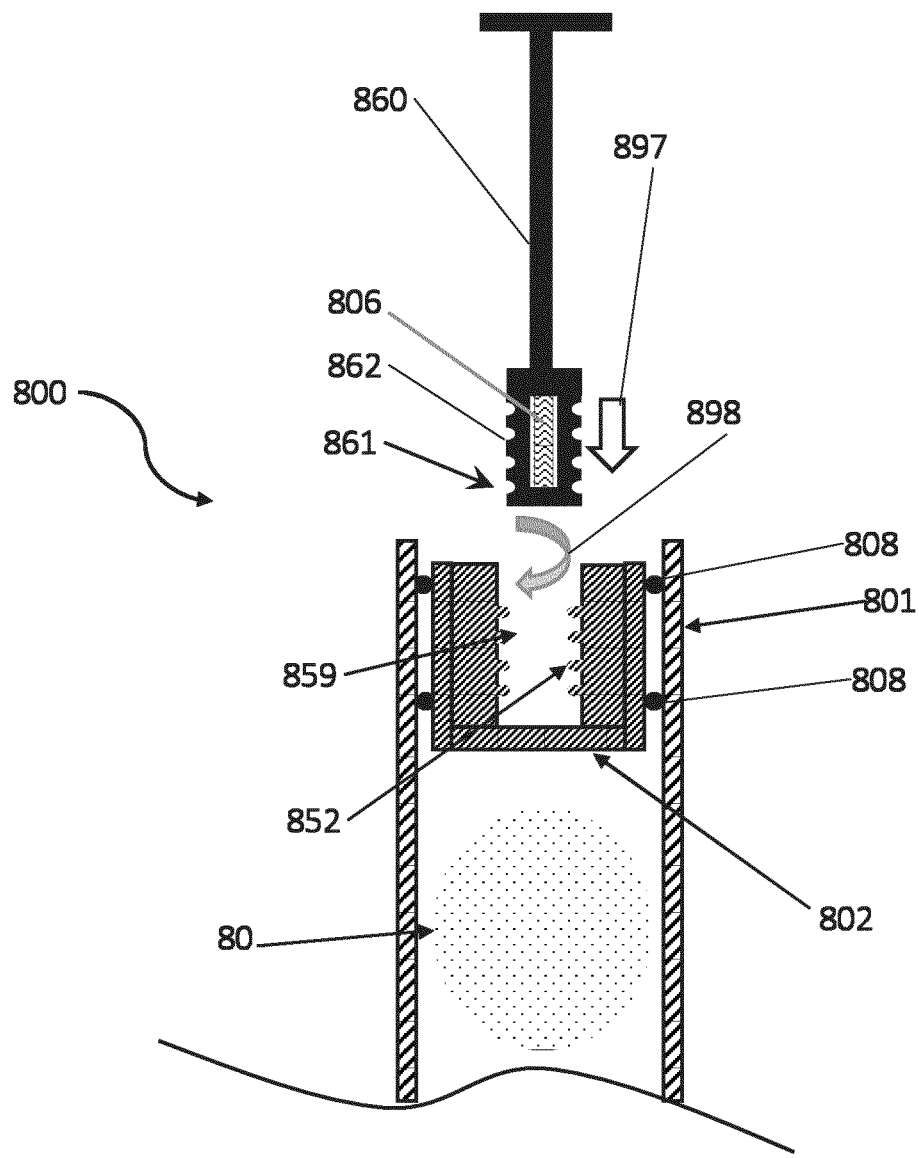
FIGS. 8A and 8B are cross-sectional views of a disposable syringe having electronics embedded into a threaded distal end of the plunger.
Figure 8B:
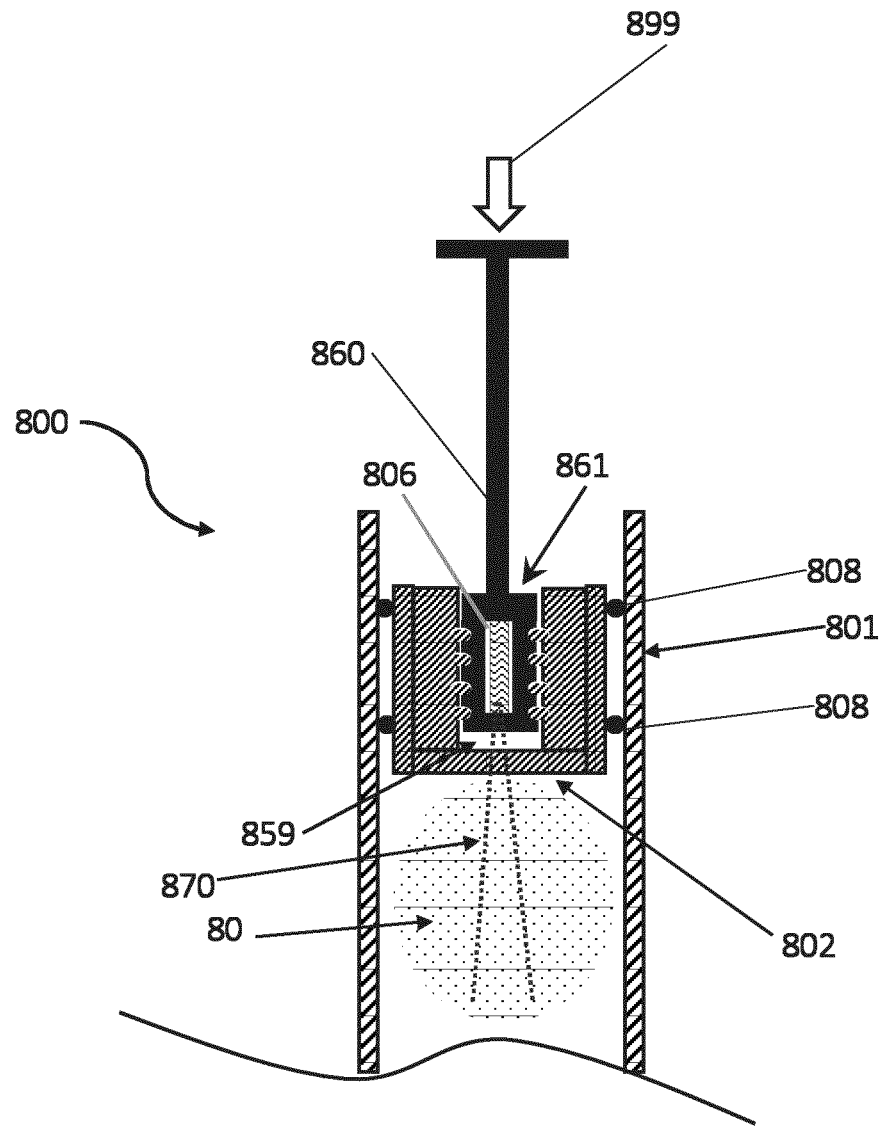

FIG. 7C is a schematic view of a distributed electronics system 700 for a medical cartridge 600 where the wireless transceiver 704, energy source 706, and sensor 708 are disposed external to the stopper 702. In this embodiment, the electronics 704, 706, and 708 are disposed in the cartridge 600 outside of the stopper 702 and may be, for example, located in a threaded rod portion of the cartridge assembly (FIGS. 8A and 8B). In this embodiment, a sensing signal output by the sensor 708 must be able to proceed through the stopper 702 and return to the sensor 708 to gather data regarding the stopper's 702 positioning. This embodiment allows the stopper to be heat sterilized, yet allows for the use of electronic components that may not withstand the heat sterilization process of the stopper.

FIG. 7D is a schematic view of a distributed electronics system 700 for a medical cartridge 600 where the wireless transceiver 704 and the sensor 708 are disposed within the stopper 702 and the energy source 706 is disposed external to the stopper 702. In this embodiment, the electronics that are disposed in the cartridge outside of the stopper (e.g. the energy source) may be, for example, located in a threaded rod portion of the cartridge assembly. Embodiments of electronics located in the threaded rod portion are shown below with respect to FIGS. 8A and 8B. This embodiment allows for the stopper to be heat sterilized, yet allows for the use of an energy source 706 that may not withstand the heat sterilization process of the stopper. The electronic components that can withstand the heat sterilization process, here the wireless transceiver 704 and the sensor 708, are embedded in the stopper to save space and/or provide an advantageous placement for position-based measurements.

FIGS. 8A and 8B are cross-sectional views of a disposable syringe 800 having electronics 862 embedded into a threaded distal end 861 of a plunger 860. The stopper 802 includes threaded features 852 extending into a central cavity 859. The distal end 861 of the plunger 860 includes corresponded threaded features 862 arranged to secure the plunger rod 860 to the stopper 802. As detailed above, the stopper 802 is sealingly engaged to a cartridge, which is shown here as a housing 801 of the syringe, using a plurality of sealing members 808 disposed around the periphery of the stopper 802. In operation, the distal end 861 of the plunger 860 is moved (e.g., arrow 897) into contact with the stopper 802, and rotated (e.g., arrow 898) into threaded engagement with the stopper 802, as shown in FIG. 8B. In this configuration, the electronics device 806 is disposed in the stopper 802 and arranged to emit a sensing signal 870 in order to, in some embodiments, determine the position of the stopper 802 within the housing 801 of the syringe 800, or to determine if an injection operation has occurred.

As shown in FIG. 8B, a force 899 is applied to the plunger 860 (e.g., by a patient or clinician operator of the syringe 800) and the plunger 860 drives the stopper 802 in the housing 801 of the syringe 800 in order to expel at least a portion of the medicament 80 from the syringe 800. One benefit of the disposable syringe 800 configuration of FIGS. 8A of 8B is the ability for the syringe housing 801 and stopper 802 to be subjected to heat sterilization prior to the introduction of the plunger 860 to the stopper 802, and thus eliminating a need to subject the electronic device 806 included in the distal end 861 of the plunger 860 to heat sterilization.

In the embodiment shown in FIGS. 8A and 8B, one or more electronic devices may be embedded in the stopper 802. The one or more embedded electronic devices may communicate with electronics device 806 disposed in the threaded distal end 861 of the plunger 860. The stopper with the at least one embedded electronic device may include a rigid shell or may be heat sterilized as discussed in relation to FIG. 2A. Another advantage of this implementation is that the electronics device 806 is outside of the sterile process. It can be manufactured more easily and cheaply in a typical manufacturing process. From a logistics perspective, introduction of the electronics device 806 may be done in a later manufacturing step and offers advantages regarding battery lifetime because the storage time can be optimized.

Figure 9:
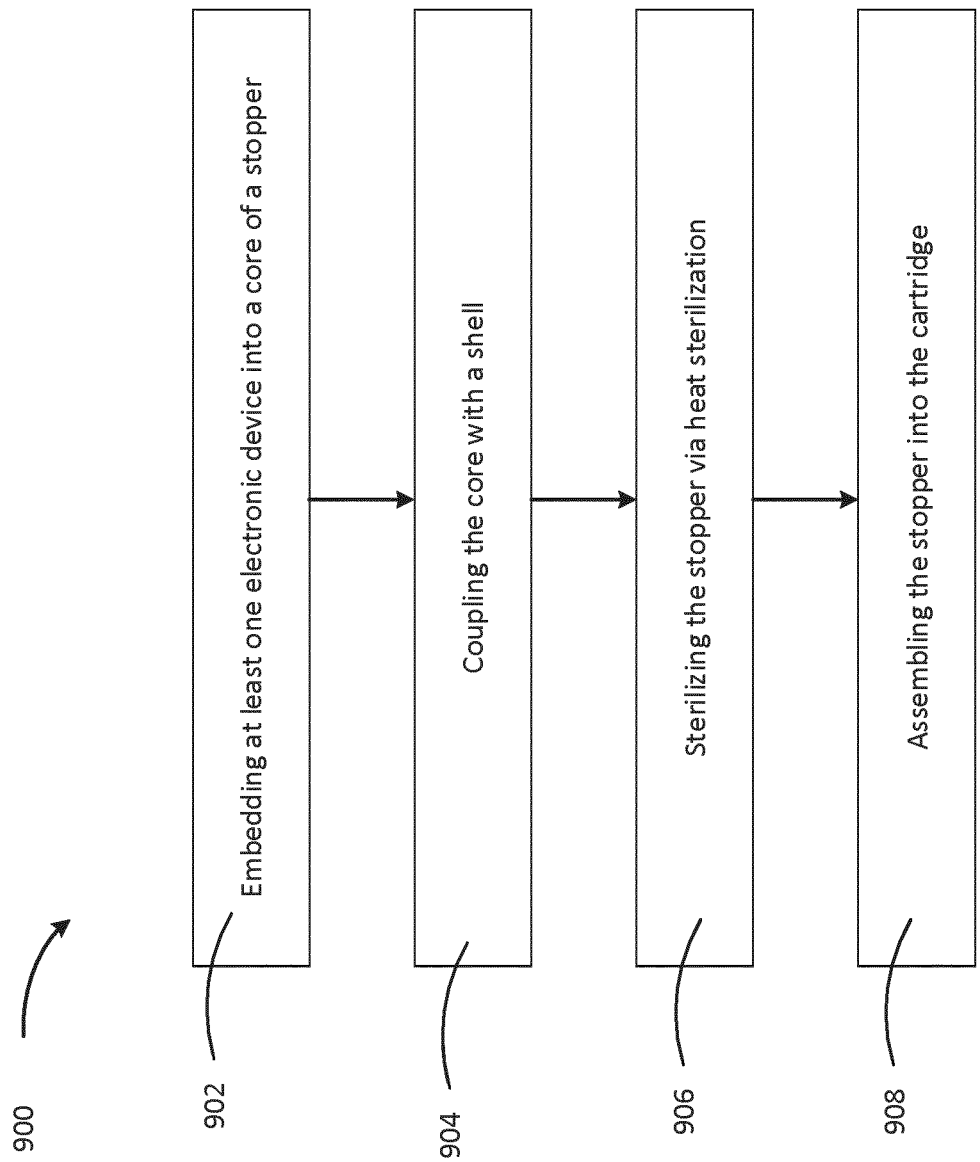
FIG. 9 is a flowchart depicting a process of manufacturing a cartridge with distributed electronic elements.

FIG. 9 is a flowchart depicting a process 900 of manufacturing a medical cartridge with distributed electronic elements. The process includes embedding 902 at least one electronic device into a core of a stopper. The types of electronic devices and their properties have been described above with respect to FIG. 2A. Additionally, the materials for manufacturing the core of a stopper have been discussed above with respect to FIG. 2A. The process also includes coupling 904 the core with a shell, the shell providing heat resistance to the at least one electronic device embedded in the core. Coupling a core with a shell may include forming a substantially inseparable, one-piece stopper as described with respect to FIGS. 2A and 3A, or may include inserting a pre-formed core into a shell creating a separable, two-piece stopper as described with respect to FIGS. 4 and 5. The process also includes sterilizing 906 the stopper via heat sterilization. In an example heat sterilization protocol, the stopper is sterilized at a temperature of at least 120 degrees Celsius for twenty to thirty minutes. The process also includes assembling 908 the stopper into the cartridge. Assembling the stopper into the cartridge creates a sealing interface to seal the medicament in the cavity of the cartridge. Additionally, upon assembling the stopper with the cartridge, other electronic components, which are not embedded in the core of the stopper, may be assembled into the cartridge.

Figure 10:
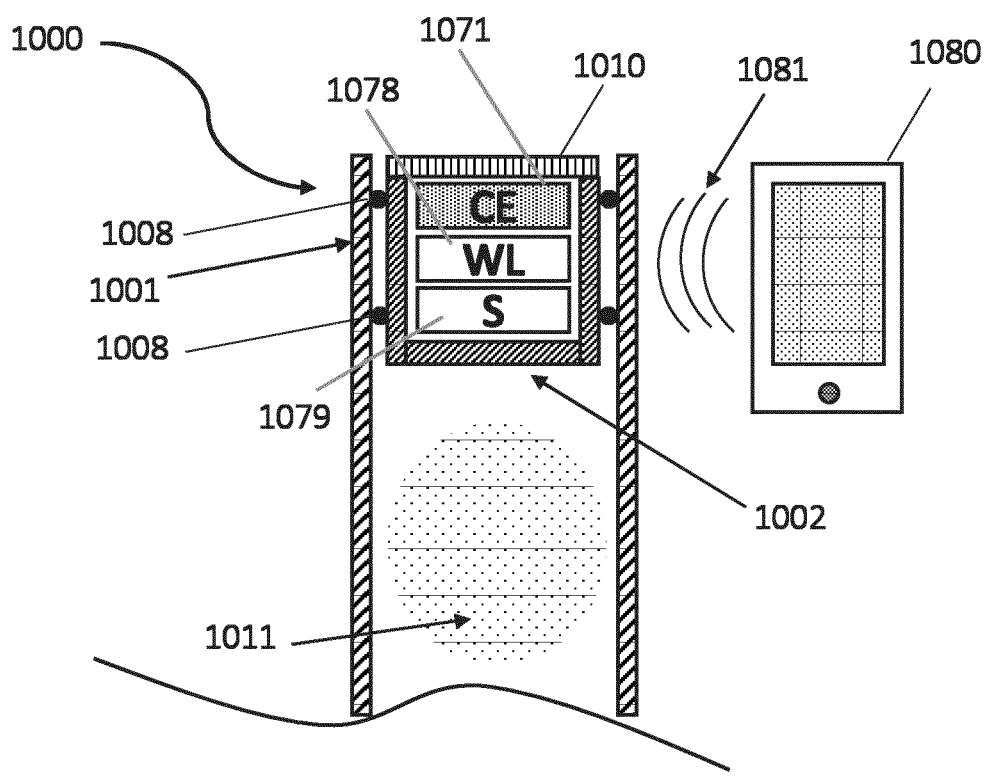
FIG. 10 is cross-sectional view of a stopper disposed within a cartridge and communicating with a wireless system.

FIG. 10 is cross-sectional view of a stopper disposed within a cartridge and powered by a wireless system. One example of an energy harvesting system is shown in FIG. 10. FIG. 10 shows a cartridge 1000 including a stopper 1002 disposed in a housing 1001 of the cartridge 1000. The stopper 1002 and sealing elements 1008 together contain a medicament 1011 in the housing 1001 and the stopper 1002 includes a plurality of sealing elements 1008 disposed around the periphery of the stopper 1002 and sealingly engaged to an inner surface of the housing 1001. The stopper 1002 also includes a cap 1010 enclosing an opening of the stopper 1002, into which an electronics assembly 1071, 1078, 1079 has been inserted. In operation, the electronics assembly 1071, 1078, 1079 is, in some embodiments, integrated with or carried by the cap 1010, whereby securing the cap 1010 to the stopper 1002 includes inserting the electronics assembly 1071, 1078, 1079 into the cavity of the stopper 1002. The electronics assembly 1071, 1078, 1079 includes a sensing device (5) 1079, a wireless device (WL) 1078, and a capacitive device (CE) 1071.

In operation, the sensing device 1079 is configured to sense the position of the stopper 1002 within the housing 1001, and the wireless device 1078 is configured to communicate with an external electronic device (not shown) in order to communicate information from the sensor device 1079. The capacitive device 1071 is configured to provide electric power to the sensing device 1079 and the wireless device 1078 by way of wireless inductive charging from a wireless signal 1081 located in proximity to the cartridge 1000. In some embodiments, the capacitive device 1071 includes capacitive circuitry that is configured receive power wirelessly from, for example, a smartphone 1080 via a nearfield communication protocol (NFC) signal 1081, or by a typical wireless charging device with other means of inductive loading, in order to provide enough energy for initiating and performing measurements with the sensing device 1079 in the cartridge 1000 and for transmitting back the results using the wireless device 1078.

FIGS. 11A and 11B are cross-sectional views of a stopper disposed within a cartridge and powered by a piezoelectric system. Another example of an energy harvesting system is the use of a piezo technology to collect energy from the mechanical forces occurring in the between the stopper and plunger (or, for example the cartridge-stopper-threaded rod system of FIGS. 11A and 11B) during, for example, injector handling or an injection operation, to provide enough energy for initiating and performing the measurement in the cartridge and for transmitting back the results. FIG. 11A shows a cartridge 1100 having a stopper 1102 disposed in a housing 1101 of the cartridge 1100 and plunger 1160 advancing (e.g., along arrow 1197) to contact a cap 1110 of the stopper 1102. The stopper 1102 and sealing elements 1108 together contain a medicament 1111 in the housing 1101 and the stopper 1102 includes a plurality of sealing elements 1108 disposed around the periphery of the stopper 1102 and sealingly engaged to an inner surface of the housing 1101. The cap 1110 encloses an opening of the stopper 1102, into which an electronics assembly 1172, 1178, 1179 has been inserted, and the cap 1110 is configured to at least partially deflect under the force of the plunger 1160 or otherwise enable a transfer for force from the plunger to a portion of the electronics assembly 1172, 1178, 1179. In operation, the electronics assembly 1172, 1178, 1179 is, in some embodiments, integrated with or carried by the cap 1110, whereby securing the cap 1110 to the stopper 1102 includes inserting the electronics assembly 1172, 1178, 1179 into the cavity of the stopper 1102. The electronics assembly 1172, 1178, 1179 includes a sensing device (S) 1179, a wireless device (WL) 1178, and a piezoelectric element (PE) 1172.

In operation, the sensing device 1179 is configured to sense the position of the stopper 1102 within the housing 1101, and the wireless device 1178 is configured to communicate with an external electronic device (not shown) in order to communicate information from the sensor device 1179. The piezoelectric element 1172 is configured to provide electric power to the sensing device 1179 and the wireless device 1178 by way of transforming a portion of the force applied to the stopper 1102 into electric energy. As shown in FIG. 11B, the piezoelectric element 1172 is transformed from a position 1198 of FIG. 8A to a deflected position 1199 of FIG. 8B by the force applied to the cap 1110 by the plunger 1160 (during the motion indicated by arrow 1197). The transformation of the piezoelectric element 1172 from position 1198 to the deflected position 1199 absorbs energy and converts a portion of it to electric energy.

Figures 12A, 12B:
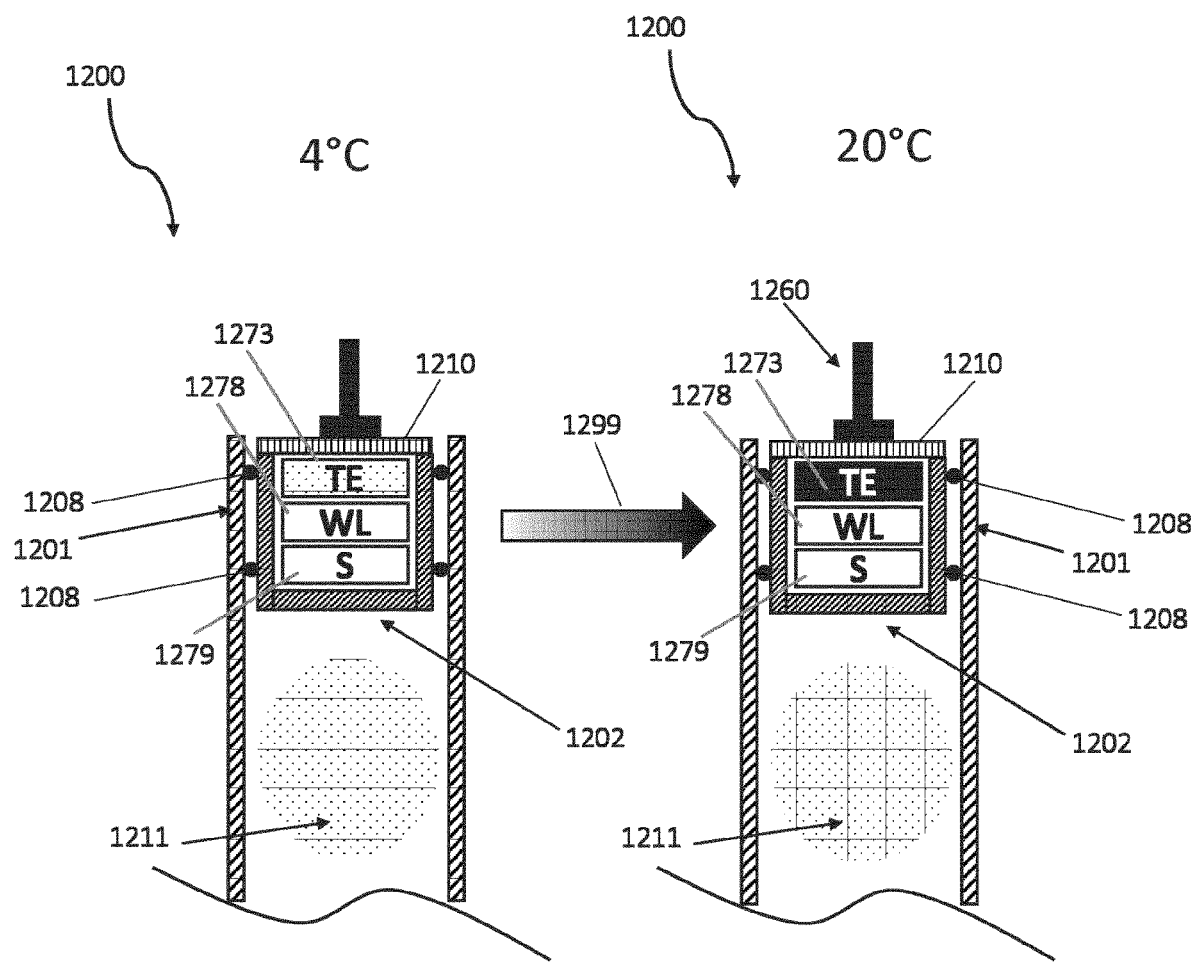
FIGS. 12A and 12B are cross-sectional views of a stopper disposed within a cartridge and Peltier thermoelectric device.

FIGS. 12A and 12B are cross-sectional views of a stopper disposed within a cartridge and including a Peltier thermoelectric device. Another example an integrated energy harvesting device is the inclusion of a thermoelectric element (TE), such as a Peltier element to convert the temperature differences between refrigeration of the pen or injector during storage and it warming up into electric energy to provide enough energy for initiating and performing the measurement in a cartridge of the injector/pen and for transmitting back the results. FIG. 12A shows a cartridge 1200 being stored in a low temperature environment (e.g., 4° C.) and having a stopper 1202 disposed in a housing 1201 of the cartridge 1200 and plunger 1120 positioned against a cap 1210 of the stopper 1202. The stopper 1202 and sealing elements 1208 together contain a medicament 1211 in the housing 1201 and the stopper 1202 includes a plurality of sealing elements 1208 disposed around the periphery of the stopper 1202 and sealingly engaged to an inner surface of the housing 1201. The cap 1210 encloses an opening of the stopper 1202, into which an electronics assembly 1273, 1278, 1279 has been inserted, and the cap 1210 or stopper 1202 is configured to at least partially transfer thermal energy to the electronics assembly 1273, 1278, 1279. In operation, the electronics assembly 1273. 1278, 1279 is, in some embodiments, integrated with or carried by the cap 1210, whereby securing the cap 1210 to the stopper 1202 includes inserting the electronics assembly 1273, 1278, 1279 into the cavity of the stopper 1202. The electronics assembly 1273, 1178, 1179 includes a sensing device (S) 1279, a wireless device (WL) 1278, and a thermoelectric element (TE) 1273.

In operation, the sensing device 1279 is configured to sense the position of the stopper 1202 within the housing 1201, and the wireless device 1278 is configured to communicate with an external electronic device (not shown) in order to communicate information from the sensor device 1279. The thermoelectric element 1273 is configured to provide electric power to the sensing device 1279 and the wireless device 1278 by way of generating energy when the temperature of the thermoelectric element changes. As shown in FIG. 12B, the cartridge 1200 is moved to a relatively higher temperature environment (e.g., 20° C.) and the thermoelectric element 1273 is heated by absorbing thermal energy from the environment outside the cartridge 1200 (during the temperature transition indicated by arrow 1299). The absorption of thermal energy by the thermoelectric element 1273 generates electric energy to power, for example, the sensing device 1279 and the wireless device 1278. The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The various materials from which the shell and the core could be produced as well as the various electronic devices that may be embedded in the core are described above with respect to FIG. 2A. Additionally, the material for the shell may be medical grade with the stopper being configured to come in contact with the medicament.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some embodiments, the chamber may be designed to store a drug for at least one day (e.g., 1 to at least 30 days). In some embodiments, the chamber may be designed to store a drug for about 1 month to about 2 years. Storage may occur at room temperature (e.g., about 20° C.), or refrigerated temperatures (e.g., from about −4° C. to about 4° C.). In some embodiments, the drug container may be or may include a dual-chamber cartridge configured to store two or more components of a drug formulation (e.g., a drug and a diluent, or two different types of drugs) separately, one in each chamber. In such embodiments, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the present disclosure have been described. Nevertheless, it will be understood that various modifications may be made without departing from the spirit and scope of the present disclosure. Accordingly, other embodiments are within the scope of the following claims.

REFERENCE NUMERALS 80 medicament
100 injection device
104 cartridge housing
106 drive mechanism
108 stopper
109 needle
110 housing
111 injection button
112 dosage knob
113 dosage window
114 cartridge
115 needle assembly
116 inner needle cap
117 outer needle cap
118 cap
122 electronic component
124 electronic component
200 stopper
202 rigid shell
204 core
206a electronic device
206b electronic device
206c electronic device
208 sealing element
300 stopper
302 soft shell
304 rigid core
306a electronic device
306b electronic device
306c electronic device
308 sealing element
400 stopper
402 rigid shell
404 core
406a embedded electronic device
406b embedded electronic device
406c embedded electronic device
408 sealing element
410 cover
500 stopper
502 soft shell
504 rigid insertable core
506a embedded electronic device
506b embedded electronic device
506c embedded electronic device
508 sealing element
600 cartridge
602 cartridge housing
604 cap
700 distributed electronics system
702 stopper
704 wireless transceiver
706 energy source
708 sensor
710 connector
800 disposable syringe
801 housing
802 stopper
806 electronic device
808 sealing member
852 threaded features
859 central cavity
860 plunger
861 distal end
862 corresponded threaded features
870 sensing signal
897 arrow
898 arrow
899 force
900 process
902 embedding electronic device
904 coupling core with shell
906 sterilizing stopper
908 assembling stopper into cartridge
1000 cartridge
1001 housing
1002 stopper 1008 sealing element
1010 cap
1011 medicament
1071 capacitive device (CE)
1078 wireless device (WL)
1079 sensing device (S)
1081 wireless signal
1080 smartphone
1100 cartridge
1101 housing
1102 stopper
1108 sealing element
1110 cap
1111 medicament
1160 plunger
1172 piezoelectric element (PE)
1178 wireless device (WL)
1179 sensing device (S)
1197 arrow
1198 position
1199 deflected position
1200 cartridge
1201 housing
1202 stopper
1208 sealing element
1210 cap
1211 medicament
1260 plunger
1273 thermoelectric element (TE)
1278 wireless device (WL)
1279 sensing device (S)
1299 arrow

The invention claimed is:

1. A stopper configured to be disposed within a medical cartridge, the stopper comprising:
 a shell defining a cavity, the shell comprising a first portion and a second portion, the first portion and the second portion comprising different materials;
 a core arranged within the cavity; and
 at least one electronic device embedded within the core, wherein the at least one electronic device comprises a sensor configured to receive a reflected sensing signal that has passed through the shell,
 wherein the shell is configured to thermally insulate the at least one embedded electronic device such that the entire stopper is heat sterilizable at a temperature of at least 120 degrees Celsius.

2. The stopper of claim 1, wherein the stopper is configured to be heat sterilized at the temperature of at least 120 degrees Celsius for at least 20 minutes.

3. The stopper of claim 1, wherein the shell is substantially rigid and the core is substantially soft, the core being softer than the shell.

4. The stopper of claim 3, further comprising a cover configured to interface with the shell such that a mechanical force is transmittable through the shell with limited compression of the core.

5. The stopper of claim 1, wherein the sensor comprises a piezoelectric device.

6. The stopper of claim 1, wherein the at least one embedded electronic device comprises an energy source.

7. The stopper of claim 1, wherein the shell and the core are inseparable.

8. The stopper of claim 1, wherein the core comprises a heat resistive coating.

9. The stopper of claim 8, wherein the heat resistive coating comprises polytetrafluoroethylene.

10. The stopper of claim 1, wherein the at least one electronic device comprises a transmitter configured to transmit a sensing signal through the shell and the reflected sensing signal is a reflected portion of the sensing signal.

11. The stopper of claim 10, wherein the medical cartridge is configured to reflect the sensing signal to generate the reflected sensing signal.

12. The stopper of claim 1, wherein the at least one electronic device comprises a processor in communication with the sensor.

13. The stopper of claim 12, wherein the processor is configured to determine a state of the medical cartridge comprising information regarding at least one of a level of medicament in the medical cartridge and a position of the stopper.

14. The stopper of claim 12, wherein the processor is configured to determine a volume of dose administered from the medical cartridge based on the received sensing signal.

15. The stopper of claim 1, wherein the at least one electronic device comprises a transceiver configured to communicate with the sensor and communicate with an external electronic device.

16. The stopper of claim 15, wherein the transceiver is configured to communicate information of the received sensing signal to the external electronic device, and the external electronic device is configured to determine a state of the medical cartridge based on the communicated information, wherein the state of the medical cartridge comprises at least one of a level of medicament in the medical cartridge and a position of the stopper.

17. The stopper of claim 1, wherein the at least one electronic device comprises a piezoelectric element configured to provide electrical power to the sensor based on a force applied to the stopper.

18. The stopper of claim 1, wherein the at least one electronic device comprises a thermoelectric element configured to provide electrical power to the sensor based on a temperature difference of the stopper between a first time and a second time.

19. The stopper of claim 1, wherein the at least one electronic device is configured to determine information based on the received reflected sensing signal after the entire stopper has been heat sterilized at the temperature of at least 120 degrees Celsius.

20. An injection device comprising:
 a housing;
 a cartridge disposed with the housing, the cartridge containing a medicament;
 a stopper disposed within the cartridge, the stopper comprising
  a shell defining a cavity, the shell comprising a first portion and a second portion, the first portion and the second portion comprising different materials;
  a core arranged within the cavity; and
  at least one electronic device embedded within the core,
  wherein the shell is configured to thermally insulate the at least one embedded electronic device such that the entire stopper is heat sterilizable at a temperature of at least 120 degrees Celsius;
 a dose dial configured to set a dosage of the medicament;
 a plunger rod slidably disposed within the housing, the plunger rod configured to force the stopper to move distally within the cartridge to expel the set dosage of the medicament from the injection device.

21. The injection device of claim 20, wherein the at least one electronic device comprises a sensor and wherein the sensor is configured to receive a reflected sensing signal that has passed through the shell.

22. The injection device of claim 21, wherein the at least one electronic device is configured to determine information based on the received reflected sensing signal after the entire stopper has been heat sterilized at the temperature of at least 120 degrees Celsius.

* * * * *